(12) United States Patent
Kosiba et al.

(10) Patent No.: US 6,366,807 B1
(45) Date of Patent: *Apr. 2, 2002

(54) ELECTRODE SYSTEM IN IONTOPHORETIC TREATMENT DEVICES

(75) Inventors: Wojciech A. Kosiba; Dean L. Kellogg, both of San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/659,674

(22) Filed: Sep. 11, 2000

Related U.S. Application Data

(62) Division of application No. 08/826,706, filed on Apr. 7, 1997, now Pat. No. 6,119,037, which is a division of application No. 08/469,130, filed on Jun. 6, 1995, now abandoned.

(51) Int. Cl.$^7$ .................................. A61N 1/30
(52) U.S. Cl. .................. 604/20; 604/21; 604/501
(58) Field of Search .................. 604/20–21, 264, 604/280; 607/115, 116, 122, 123, 105, 152, 153, 148, 129, 36; 606/41, 95

(56) References Cited

U.S. PATENT DOCUMENTS

| | | | |
|---|---|---|---|
| 4,019,510 A | 4/1977 | Ellis ........................ 128/172.1 |
| 4,027,393 A | 6/1977 | Ellie et al. ..................... 32/10 |
| 4,411,648 A | 10/1983 | Davis et al. ................... 604/21 |
| 4,717,379 A | 1/1988 | Ekholmer .................... 604/43 |
| 4,950,229 A | * 8/1990 | Sage, Jr. |
| 5,154,165 A | 10/1992 | Elliott et al. ................. 128/419 |
| 5,188,738 A | 2/1993 | Kaali et al. .................. 210/748 |
| 5,260,020 A | 11/1993 | Wilk et al. ..................... 422/22 |
| 5,324,275 A | 6/1994 | Raad et al. ................... 604/265 |
| 5,328,451 A | 7/1994 | Davis et al. ................... 604/20 |
| 5,515,848 A | * 5/1996 | Corbett, III et al. |
| 6,002,956 A | * 12/1999 | Schaer |
| 6,119,037 A | * 9/2000 | Kellogg et al. |

FOREIGN PATENT DOCUMENTS

| | | |
|---|---|---|
| DE | 32 40 838 | 10/1984 |
| FR | 2516388 | 11/1981 |
| GB | 2 063 072 | 6/1981 |

OTHER PUBLICATIONS

International Search Report dated Oct. 4, 1996 (UTFK:249P).

\* cited by examiner

*Primary Examiner*—Mark Bockelman
(74) *Attorney, Agent, or Firm*—Fulbright & Jaworski

(57) ABSTRACT

This invention relates to the field of medical devices employing electrophoresis to combat bacterial colonization. More particularly, it relates to an apparatus and method of providing an electrophoresis-type medical device that mitigates the burning of surrounding biological tissue. This invention uses grooves in the contact surface of the medical device for containing the electrodes which cause the electrophoresis to occur. The grooves allow the electrodes to contact biological fluid without contacting and hence burning the surrounding biological tissue. Through the use of this invention it is possible to provide an electrophoresis-type medical device while minimizing the burning of surrounding tissue.

12 Claims, 2 Drawing Sheets

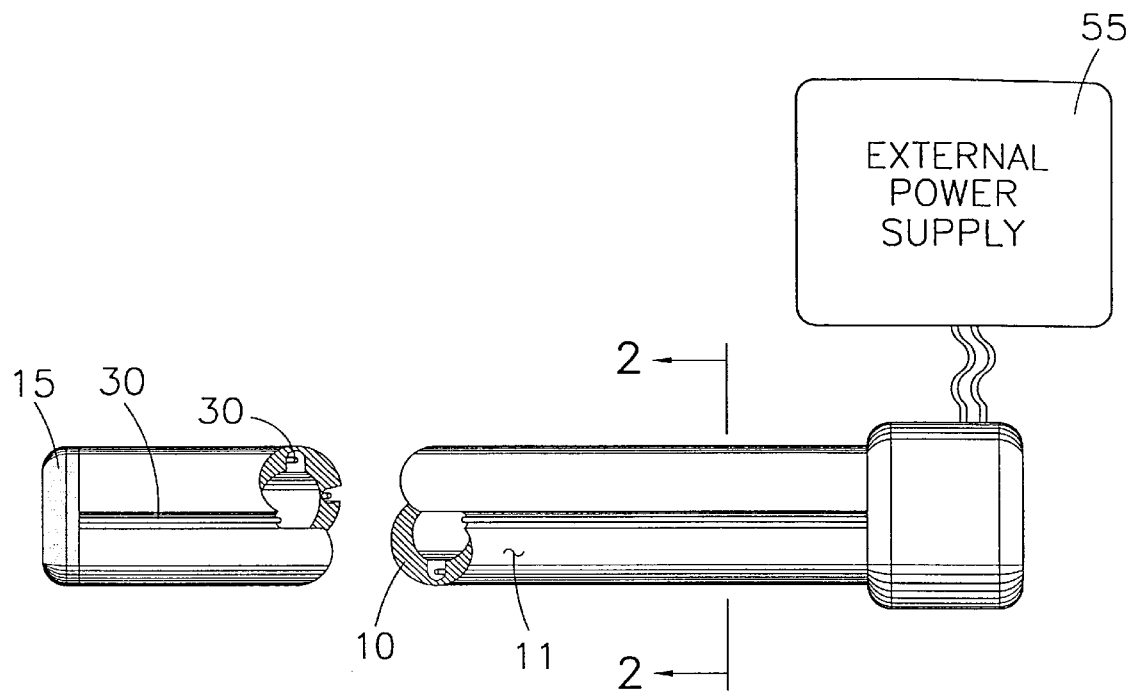
Fig. 3.
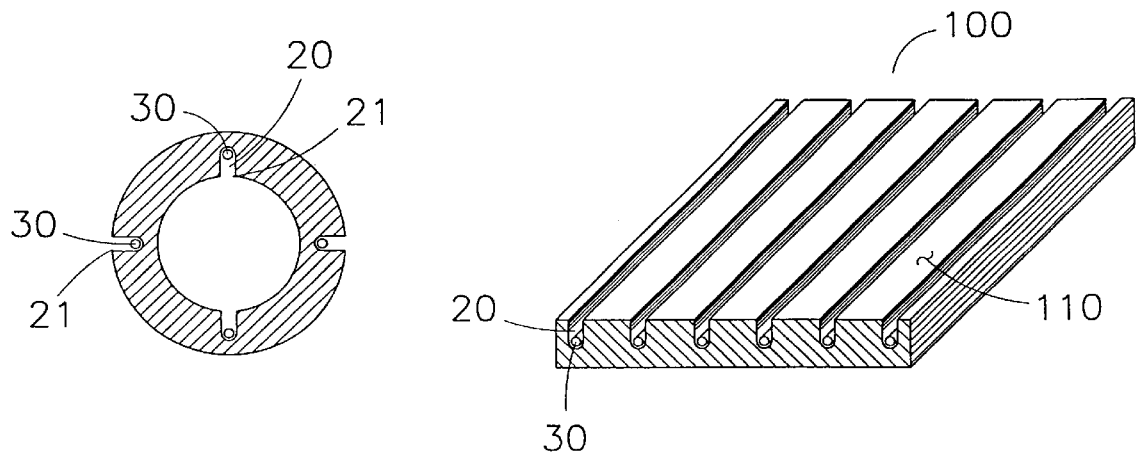
Fig. 4.
Fig. 5.

ELECTRODE SYSTEM IN IONTOPHORETIC TREATMENT DEVICES

This is a divisional of application Ser. No. 08/826,706, filed Apr. 7, 1997, U.S. Pat. No. 6,119,037 which was a divisional of application Ser. No. 08/469,130, filed Jun. 6, 1995 now abandoned.

BACKGROUND OF THE INVENTION

1. Field of the Invention

The present invention relates to an electrode system embedded in an electrically insulating material which in various configurations may be added to existing medical devices such as catheters, prosthetic joints and treatment pads. The present invention combats infections associated with long term use of medical devices.

2. Discussion of the Prior Art

Certain medical treatments require placement of a medical device in a patient's body. These medical devices sometime provide a path for infection by microorganisms which can contaminate the devices. Such contamination may occur, for example, when the devices are inserted through the skin. The microorganisms, bacteria, and the like tend to migrate along the external or internal surfaces of the devices and thereby give rise to infections. Likewise, other medical devices such as prosthetic joints and treatment pads require long-term placement in a patient's body and may lead to infections.

For example, bacterial infections of indwelling vascular catheters can be a source of morbidity and even mortality in patients. Such infections are estimated to occur in three to five percent of patients with central venous catheters. Catheter related bacteremia can add 7 to 14 days of hospitalization time and costs, and is often associated with death in these occurrences. To reduce the chances of such infection, surgical placement of tunneled central venous catheters is often done; however, this procedure dramatically raises the costs of catheterization.

Increasing amounts of data indicate that low amperage electric currents are bactericidal, and catheters employing such currents have shown dramatic resistance to bacterial colonization in the laboratory. In that regard, a number of electrophoresis catheters have been suggested. One such catheter applies small DC electric currents between an electrically conductive catheter and an adjacent electrode. Unfortunately, an optimal current density tends to exist only within a small volume of tissue around the point of entrance of the catheter into a patient's body. Consequently, any microorganisms surviving beyond this small protected volume are free to migrate down the catheter.

Progress has also been made by the use of two parallel, helical electrodes on the exterior surface of a catheter, together with two parallel electrodes on the interior surface of the catheter. This system is described in U.S. Pat. No. 5,324,275, issued to Raad et al. The two external electrodes are partially embedded within the outer surface of a central portion of the catheter tube or lumen, and the two internal electrodes are partially embedded within the internal surface of a hub portion of the catheter. The proximal end of the catheter tube terminates in the hub. Energizing the two separate pairs of electrodes in the presence of a body fluid provides an oligodynamic activity.

Still another catheter design calls for a pair of electrodes to extend along the interior of a catheter lumen and to terminate at the distal orifice of the lumen. The electrodes may be embedded in the wall of the catheter and thereby insulated. They may also be uninsulated, in which case they may be embedded or imprinted along the interior wall of the catheter so as to be kept separate from one another.

It is of interest that previous electrophoresis-type medical devices do not suggest barring or restraining contact between an electrode and body tissues. Primary concerns are for separation of the electrodes from one another, and exposure of at least a portion of the electrodes to fluids present within or around a medical device.

SUMMARY OF THE INVENTION

It has now been found that while electrophoresis-type medical devices are effective in reducing infections, they unfortunately can cause other damage to surrounding tissues. In particular, contacts between the electrodes and the tissues can result in serious burns. This is especially the case when the current flow is increased to increase bactericidal action.

The present invention addresses the above problems by means of an electrode system, wherein the surfaces of the inserted medical device contain recessed grooves for receiving one or more pairs of electrodes. The recesses are such that the electrodes are kept out of contact with surrounding tissues, but the recessed grooves are also such that the electrodes are kept separate from one another while being exposed to the tissues. Energizing the electrodes thereby generates an electrophoresis effect and protects the tissues, without burning the tissues.

The present invention provides an electrode system embedded in electrically insulated material used with a medical device which is inserted into an animal or human body. The medical device is in contact with biological fluid and biological tissue and is formed in part of an electrically insulating material. Electrodes are placed into grooves on the body of the medical device so as to enable the electrodes to contact the biological fluid without contacting the surrounding biological tissue. Alternatively, the electrodes may be mounted on the medical device or only partially recessed in the body of the medical device and covered with a fine mesh which allows contact between the electrodes and biological fluid while preventing contact between the electrodes and biological tissue.

One embodiment of the present invention is a catheter which is resistant to microbial colonization. The catheter has an electrically insulated, tissue compatible tube. The exterior surface of the tube contains two or more grooves each of which holds an electrode. The electrodes and grooves are dimensioned as to allow biological fluid to contact the electrodes, while not allowing biological tissue to contact the electrodes. The catheter may also have grooves on the interior surface of the tube. As with the exterior grooves, the interior grooves and electrodes are dimensioned to allow fluid to contact the electrodes, while not allowing solid objects placed into the tube to contact the electrodes. The grooves may be straight and longitudinal relative to the catheter tube or may be helical.

Another embodiment of the present invention is an adapter that can be mated to a standard catheter that is not equipped with electrodes. The adapter is made of an electrically insulating material and may have grooves and electrodes on the exterior and/or interior surfaces. The adapter may be inserted into the standard catheter or may be inserted as a sleeve over the standard catheter. When mated to the standard catheter, the adapter can add electrophoretic antimicrobial protection to the standard catheter.

Another embodiment of the present invention is an iontophoretic treatment pad resistant to microbial colonization. The treatment pad has an electrically insulating, tissue compatible contact surface for contacting the tissue to be treated. The contact surface contains at least two grooves, each groove holding an electrode and being dimensioned as to allow biological fluid to contact said electrode in use without contact between soft biological tissue and said electrode.

BRIEF DESCRIPTION OF THE DRAWINGS

The above-recited advantages and features of the present invention, as well as others which will become apparent, may be further understood by the following more detailed description of the invention, taken together with the appended drawings, which drawings form a part of the specification. It is to be noted, however, that the appended drawings illustrate only typical embodiments of the invention and are therefore not to be considered limiting of its scope, for the invention may admit to other effective embodiments.

FIG. 3 is a partially cut away side view of one embodiment of an electrophoresis catheter adapter according to the present invention. Such an adapter can be mated to a standard non-electrophoresis catheter to add bacteriologic protection.

FIG. 4 is a cross sectional view of catheter tube taken along the section lines 2–2 in FIG. 1.

FIG. 5 is a perspective view of an iontophoretic treatment pad.

DETAILED DESCRIPTION

The present invention provides an electrode system which is embedded in electrically insulating material and used with an indwelling medical device, such as a catheter, treatment pad, or prosthesis. The electrodes are embedded or covered with a mesh screen and attached to the medical device such that the electrodes contact the surrounding biological fluid without contacting the surrounding biological tissue.

Figure 1:
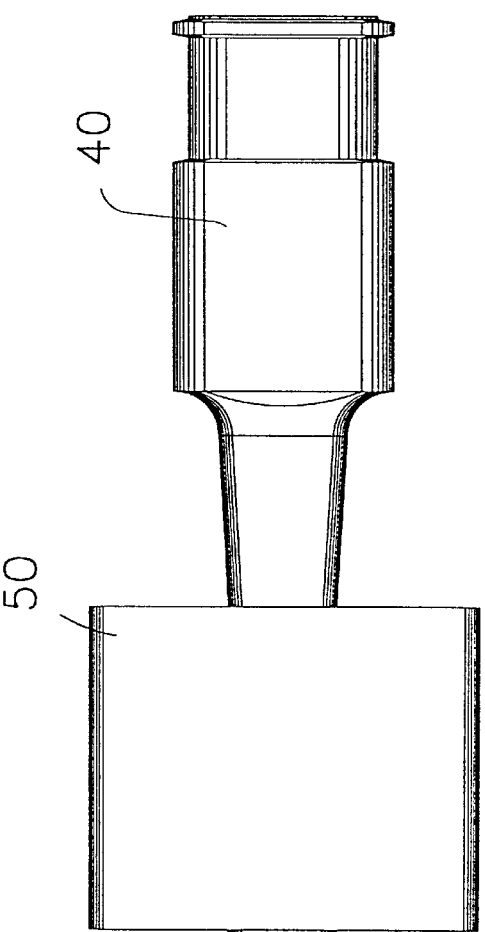
FIG. 1 is a partially cut away side view of one embodiment of an electrophoresis catheter according to the present invention.
Figure 2:
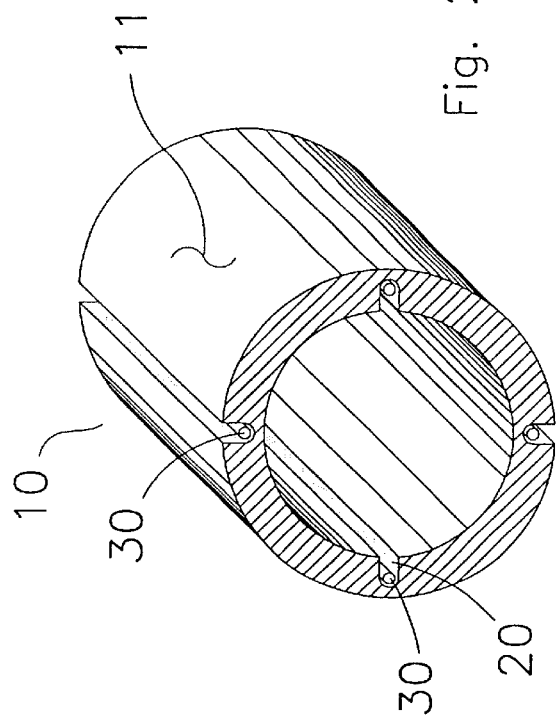
FIG. 2 is a perspective view of a cross-section of the catheter tube taken along the section lines 2—2 in FIG. 1.

FIGS. 1 and 2 illustrate an electrophoresis catheter according to the present invention which includes a catheter tube 10 having an external surface 11, recessed grooves 20, a catheter hub 40, and electrodes 30 adapted to be placed into the recessed grooves 20. The catheter tube 10 is constructed of an electrically insulating material such as polyethylene, so as not to cause a short circuit between the electrodes 30. The insertion end of the catheter tube 10 is rounded off or capped with a round edged, electrically insulating cap 15 to facilitate ease of catheter insertion. Recessed grooves 20 are formed in the external surfaces of the catheter tube 10. In one embodiment, the external grooves 20 are longitudinal and run substantially the length of the catheter tube 10. Each external groove 20 has a top edge 21 (see FIG. 4). Electrodes 30 are selected and placed into the grooves 20, so that each such electrode does not protrude out of the top 21 of its respective external groove 20, thus avoiding direct contact between the electrode and surrounding tissue. The electrical circuit is completed by the biological fluid found around the catheter that penetrates into grooves 20. Biological fluids typically act as conductors, in this instance between the two electrodes.

Grooves 20 and electrodes 30 may be placed in a similar manner within the interior surface of the catheter tube 10 as shown. Similarly, the electrode 30 should not protrude above the top of the internal grooves 20 as to avoid direct contact with any tools or other objects which may be inserted into the catheter tube 10.

FIGS. 3 and 4 illustrate an adapter sheath to add electrophoretic protection to standard catheters that are not equipped with electrodes. The adapter includes an adapter tube 10 for receiving a catheter tube in a snug relation having an external surface 11, recessed grooves 20, and electrodes 30 placed into the recessed grooves 20. The arrangement of the grooves 20 and electrodes 30 can be similar to that of the electrophoresis catheter shown in FIGS. 1 and 2. The adapter can be inserted into or over a standard catheter.

FIGS. 2 and 4 are cross-sections of the catheter or adapter tube 10 taken along the section line 2—2 in FIGS. 1 and 3, respectively. The embodiment shown depicts the use of two external, longitudinal grooves 20 and two internal, longitudinal grooves 20, each groove holding an electrode 30 such that the electrodes do not extend beyond the top 21 of the grooves 20.

The grooves in the surface of the catheter lumen preferably extend straight along the lumen; however, they may be helical and proceed along and around the lumen. In any case, they must be shaped or otherwise configured to receive and hold an electrode in a recessed position out of contact with a patient's body tissues.

The distal end of each electrode preferably extends the length of the lumen to an orifice at the distal end of the lumen. The proximal end of each lumen is adapted to be connected to a suitable external electrical power source 55 or an attached power supply 50. Each internal groove is separate from each adjacent internal groove and preferably is straight and longitudinal relative to the lumen.

In a further embodiment the electrodes are longitudinally placed on the catheter tube running substantially the length of the tube; however, other configurations are possible. For example, the electrodes and grooves may be configured in a helical or spiral arrangement around the catheter tube. Many such arrangements are feasible so long as the electrodes do not intersect and cause a short circuit. It is also possible that the paths of the grooves and electrodes may cross, but not intersect. For example, one electrode may pass underneath another electrode without making direct contact. It may also be desirable to use electrodes that do not run substantially the length of the catheter tube, depending upon the application.

The catheter tube may be formed of a flexible, non-conductive material which is compatible with body tissues and fluids. Polyolefin polymers such as polyethylene and polypropylene are especially effective materials for this service. Materials which are commonly used currently for manufacturing catheters such as latex, silicone rubber, Teflon™, and Teflon™ coated rubber are suitable for the present invention. The exterior surface of the catheter lumen is provided with at least one pair of grooves which extend the length of the lumen to an orifice at the distal end of the lumen. One groove in each such pair is adapted to receive an electrode of one polarity, and the other groove in the pair is adapted to receive an electrode of the opposite polarity. The electrodes are electrically insulated from one another by the body of the lumen. The proximal end of each electrode is adapted to be electrically coupled with a suitable source of electrical power. The distal end of the catheter tube is rounded off or capped with a round-edged, electrically insulating cap to facilitate ease of catheter insertion. At the insertion end there are no electrical connections to or between the electrodes. It is contemplated that most standard catheters may be made to work by adding suitable grooves and electrodes, or with the addition of an electrophoresis treatment adapter that incorporates grooves and electrodes.

FIG. 5 is a prospective view of an iontophoretic treatment pad. The pad 100 contains grooves 20 on the contact surface 110 of the pad which is designed to be in contact with the patient. The grooves 20 contain electrodes 30 which are adapted to be placed in the grooves 20 such that they contact biological or other electrically conductive fluid but not biological tissue.

In all embodiments, the electrodes may be constructed from any electrically conductive material which is compatible with body tissues and fluids. Carbon fibers are considered to be especially useful because they are biologically inert. Other suitable electrodes are contemplated to include gold, silver, platinum, stainless steel, iron, and copper.

The electrodes 30 may be electrified by an external power supply 55 or a power supply 50 mounted or built into the medical device. It is contemplated that either an AC or DC power supply may be employed, but a slow AC power source is presently considered to provide preferred results. The amount of current density delivered to the electrodes may vary with the size and shape of the medical device and to the particular application. The current is preferred to be between $5 \times 10^{-4}$ and $2 \times 10^{-2}$ amps per meter of electrode. Current densities below this limit appear to have no bactericidal effect, and those above this upper limit may cause tissue necrosis.

The electrodes should at all times remain out of contact with body tissue. To this end guard members attached to the contact surface of the medical device are preferably placed at intervals along each groove to keep electrodes from accidentally projecting out of the grooves. It is also contemplated that each groove may be in the form of a tunnel below the contact surface of the medical device with ports or holes enabling fluids to enter through the ports or holes into the groove.

In an alternative embodiment, the electrodes may be mounted directly to or partially embedded into the contact surface of the medical device. A fine, electrically insulating mesh screen or guard may be placed over or around the electrode. The size of the mesh openings should be small enough such that the electrode does not directly contact the surrounding biological tissue, but does directly contact the surrounding biological fluid which passes through the guard. Further, the mesh may be formed from non-conductive, biologically compatible materials. Polyolefin polymers, such as polyethylene and polypropylene, are effective materials.

In operation, the medical device is inserted into the body, and the electrodes are charged by a power source. Electricity is thereby transmitted (i.e., the circuit is completed) through the surrounding biological fluid penetrating the grooves. The resultant electrophoresis inhibits the colonization of microbodies on the medical device.

What is claimed is:

1. A medical device for insertion into an animal or human body comprising biological fluid and biological tissue, said medical device comprising:

a body member having a contact surface formed at least in part of an electrically insulating material, and configured for insertion into the animal or human body;

a first and second groove formed in the surface of said insulating material;

a first electrode recessed entirely within said first groove;

a second electrode recessed entirely within said second groove; and wherein said first and second electrodes contact said biological fluid without contacting said biological tissue;

a power supply connected to said electrodes for delivering energy thereto.

2. The medical device of claim 1, wherein said medical device comprises a sheathed catheter and said body member comprises an adapter tube for snugly receiving a catheter tube.

3. The medical device of claim 1, wherein said medical device comprises a treatment pad and said body member comprises a contact surface of said treatment pad.

4. A medical device for insertion into an animal or human body comprising biological fluid and biological tissue, said medical device comprising:

a body member having a contact surface formed at least in part of an electrically insulating material, and configured for insertion into the animal or human body;

a first and second groove defined by said body member;

a first electrode recessed at least partially within said first groove;

a second electrode recessed at least partially within said second groove; and an electrically insulating mesh screen covering said first and second electrodes, said screen comprising mesh openings preventing said electrodes from contacting said biological tissue and allowing said electrodes to contact said biological fluid.

5. The medical device of claim 4, wherein said medical device comprises a catheter and said body member comprises a catheter tube.

6. The medical device of claim 4, wherein said medical device comprises a sheathed catheter and said body member comprises an adapter tube for sungly receiving a catheter tube.

7. The medical device of claim 4, wherein said medical device comprises a treatment pad and said body member comprises a contact surface of said treatment pad.

8. The medical device of claim 4, wherein said first electrode is recessed entirely within said first groove, and wherein said second electrode is recessed entirely within said second groove.

9. The medical device of claim 4, wherein said screen comprises a polyolefin polymer.

10. The medical device of claim 4, wherein said first and second grooves extend longitudinally along said body member.

11. The medical device of claim 4, wherein said first and second grooves extend in a helical pattern along said body member.

12. A method of providing iontophoretic treatment to a patient which comprises inserting a medical device as defined in claim 4 into said patient and supplying electric current to said electrodes.

* * * * *